_United States Patent_ [19]

Petricciani et al.

[11] 4,040,905

[45] Aug. 9, 1977

[54] SUB-HUMAN PRIMATE DIPLOID CELL LINES AS SUBSTRATES FOR VIRUS VACCINE PRODUCTION

[75] Inventors: John C. Petricciani, Washington, D.C.; Hope E. Hopps, Silver Spring; Douglas E. Lorenz, Bethesda, both of Md.; Paul J. Vasington; Roslyn E. Wallace, both of Pearl River, N.Y.

[73] Assignee: The United States Government, Washington, D.C.

[21] Appl. No.: 193,176

[22] Filed: Oct. 27, 1971

[51] Int. Cl.² .............................................. C12K 9/00
[52] U.S. Cl. ..................................................... 195/1.8
[58] Field of Search ................... 424/89; 195/1.1, 1.8

[56] References Cited

U.S. PATENT DOCUMENTS 3,651,212   3/1972   Meyer et al. .......................... 424/89

OTHER PUBLICATIONS

Tyndall et al., _J. Bacteriology_, vol. 85, pp. 1339–1345, 1963.

_Primary Examiner_—Sam Rosen

[57] ABSTRACT

Sub-human primate diploid cell lines suitable for virus vaccine production are disclosed as well as the production of the cultures. In particular, monkey diploid cell lines are disclosed.

1 Claim, No Drawings

SUB-HUMAN PRIMATE DIPLOID CELL LINES AS SUBSTRATES FOR VIRUS VACCINE PRODUCTION

This invention relates to the production of tissue cultures, and more particularly, this invention relates to the production of sub-human primate diploid cell cultures.

Antivirus vaccines have been prepared by attenuating the virus strains by serieal passages through various substrates. For instance, certain vaccines could be prepared by passage through living animals or eggs. Such methods. however, have been found to be disadvantageous due to the possibility of introducing adventitous agents and the like.

In order to avoid the disadvantages inherent in these previous methods of preparing vaccine, methods were developed for using tissue cultures as substrates for the virus strains. In particular, a largeproportion of the viral vaccines licensed for human use in the United States is prepared from primary cell cultures derived from monkeys, chicks, ducks or rabbits. All of these tissue sources with the exception of monkeys come from closed specific pathogen-free breeding colonies. Monkeys whose tissues will be used for vaccine production are held in quarantine for at least six weeks but cross-infection among these animals can occur and their use poses many practical problems as well as certain theoretical risks. Additonally, human diploid cell lines are also used in foreign countries. The disadvantages of the primary cell cultures are manifest. These disadvantages include possible latent viral agents, depletion of the animal supply, and inability to thoroughly evaluate the cells before use. For example, the clinical experience with viral vaccines produced from the primary monkey kidney cell cultures has been overwhelmingly successful. Nevertheless, it clearly would be an improvement to produce vaccines in a cell substrate which itself had been extensively studied and characterized as being free of any known microbial agent.

For these reasons, the next step in the art began with the suggestion that production of vaccine in primary culture be converted to production in a well-characterized cell system as human diploid cell line WI38. Considerable research has been performed toward the use of human diploid cell lines. This research eventually led to the use of human diploid cell cultures for virus vaccine production in foreign countries. The initial work was reported by Hayflick et al., *Exp. Cell Res.*, 25 585 (1961). Various methods have been developed after the original work by Hayflick et al., which have provided improved techniques. For instance, in U.S. Pat. No. 3,450,598, granted to John A. Welsh et al., on June 17, 1969, for Method For Cell Propagation, there is disclosed a method for producing tissues cultures using a roller tube. This patent discloses the use of the method for human diploid cell cultures as well as a number of primary cells, both of human orgin and of sub-primate origin.

The morphologic and karyotypic stability of human diploid cells, their susceptibility to human viruses, and their freedom from detectable viral agents has demonstrated the general safety and economic practicality of using pre-tested diploid cell lines as substrates for virus vaccines. On the other hand, certain disadvantages have been found to exist in human diploid cell strains. These advantages include the inability to do in vivo testing of the cells in a normal population of the homologous species. Addtionally, there is the possiblity of latent human agents being present in the cells and, of course, eventual depletion of the supply of cells because of their finite life span.

Accordingly, it is primary object of the present invention to provide a cell culture for virus vaccine production which is free of the aforementioned disadvantages of primary cell cultures and human diploid cell cultures.

It is another object of the present invention to provide a cell culture for virus vaccine production comprising sub-human primate diploid cells.

It is a further object of the present invention to provide a culture for virus vaccine production comprising monkey diploid cells.

It is yet another object of the present invention to provide a method of culturing virus vaccines in sub-human primate diploid cells.

It is still another object of the present invention to provide a virus vaccine by culturing the same in a substrate of sub-human primate diploid cells.

This invention will be better understood, and objects other than those set forth above will become apparent, when consideration is given to the following detailed description thereof.

Consistent with the foregoing objects, and according to the preferred embodiment of the present invention, a cell culture is made using diploid cells obtained from monkeys. While the present invention will be described in detail by reference to the preferred embodiment, it should be distinctly understood that the invention is not limited thereto.

Before proceeding with the detailed description of the present invention by reference to the preferred embodiment wherein cell cultures are made from monkey diploid cells, consideration should be given to another aspect of the prior art. More specifically, a line of green monkey kidney cells, denoted BSC-1, has been reported in the literature and sold commercially. At one time, as indicated in the catalog of a commercial supplier, BSC-1 was listed with diploid cell strains, although with the notation that it is heteroploid with a low split ratio. In fact, it was subsequently proven that the BSC-1 line developed immortality and by passages 75 had obvious neoplastic-like morphologic changes and a polyploid chromosomal configuration (Forman et al, *Proc. Soc. Exp. Biol Med.*, 131, 1060 (1969).

PROCEDURES

Monkeys

Pregnant rhesus monkeys (*Macaca mulatta*) were obtained through commercial sources from Delhi, India and were held in isolation for six weeks after arrival. African green monkeys (*Cercopithecns aethiops*) were selected from the breeding colony at Bionetics Research Laboratories in Kensington, Md. All monkeys were skin tested for tuberculosis and examined for viremia and serum antibodies to simian viruses: ($SA_1$), ($SV_{40}$), foamy virus types I and II (FV1and FVII), cytomegalovirus (CMV), as well as poliovirus types I, II and III, measles and rubella virus.

TABLE I

| | | VIRAL ANTIBODY TITERS* OF SERA OF PREGNANT MONKEYS | | | | | | |
|---|---|---|---|---|---|---|---|---|
| | | SV-40 | FV-I | FV-II | CMV | POLIO | MEASLES | RUBELLA |
| RHESUS TITER RANGE | # POSITIVE/TOTAL | 9/19 | 19/19 | 8/19 | 19/19 | 0/10 | 7/11 | 1/6 |
| | 1:16–1:64 | 1:32–1:64 | 1:4–1:64 | 1:20–1:320 | — | 1:8–1:128 | 1:8 | |
| AFRICAN GREEN | # POSITIVE/TOTAL TITER RANGE | 0/33 — | 32/32 1:8–1:64 | 32/32 1:16–1:64 | 33/33 1:10–1:640 | 0/33 —1:- 4–1:64 | 21/33 1:4–1:10 | 4/32 |

*Reciprocal of serum endpoint dilution

Although animals free of overt illness and viremia could be selected, no monkeys were free of antibodies to all viruses tested. Viral titers of <4 were considered negative. Of 19 rhesus monkeys 9 were positive for antibody to $SV_{40}$, 8 positive for antibody to FVII and all had antibodies to FVI and CMV. Few had significant antibody levels to human polio, measles and rubella virusess.

Of 33 AG monkeys, none had antibodies to $SV_{40}$ or poliovirus, although all had antibodies to FVI. FVII and CMV, and some showed hemagglutination inhibiting antibodies to measles and rubella. Animals chosen for the project had low levels of antibody to FV types I and II and CMV.

Culture Medium

Medium used in initiating and maintaining cell cultures was Eagle's Minimum Essential Medium (MEM) containing non-essential amino acids (H. Eagle, *Science*, 130, 432 (1959), vitamins and glutamine at twice the usual concentration, and horse serum or bovine fetal serum (BFS) at 10%concentration. MEM was prepared in our laboratory during the early stages of the work and later purchased in bulk as powdered medium from Grand Island Biological Co., Grand Island, N.Y., pretested and found satisfactory for the support of colony growth of small populations of human cells, strain HeLa and diploid lung fibroblasts, strain Led 130. Media were prepared in twice glass-distilled water, Millipore filered, sterility tested and stored in +4° C, except for vitamins and glutamine which were held as 100X concentrates at −20° C. Separately filtered lots of media were labeled A and B for use on a corresponding series of each line.

Approximately 140 ml. of sterile filtered BFS representing 2 pooled lots and 18 liters of 1 lot were purchased respectively from Reheis Chemical Co., Chicago, Ill. and Hyland Laboratories, Los Angeles. These sera had been prepared in these laboratories and found free of neutralizing antibodies for measles, rubella and polioviruses, and viruses cytopathic for bovine embryonic kidney cell cultures by inoculating 0.5 ml. undiluted serum into each of 5 culture tubes which were incubated and observed for cytopathology during 2 weeks. Sera were also tested and found satisfactory for the propagation of chick embryo fibroblasts through 3 successive cell subcultures, and for the support of colony growth of small populations of HeLa and Led 130 cells. Horse serum was collected from breedings of a normal, healthy female horse obtained in 1959 at 12 years of age, immunized against tetanus and held at Lederle Laboratories until 1963 as a source of normal horse serum. Horse serum was passed through a Millipore filter; this serum was tested for bacteria, fungi and mycoplasma, inactivated at 56° C for 30 minutes and stored at −20° C.

MEM supplemented with BFS at 5% concentration was also "conditioned" by incubation of 200 ml. volumes over primary monolayer cultures of rhesus monkey kidney cells in culture bottles having a floor area of 542 cm². The primary cultures were prepared from kidneys of rhesus monkeys serologically screeened for viral antibodies After 18 hours incubation at 37° C, the medium was recovered, Millipore filered and stored at −20° C.

Complete medium was prepared by combining serum, MEM and vitamin-glutamine concentrates separately into A and B batches, aseptically dispensing, sterility testing for bacteria and fungi, and storage at +4° C at least 7 days prior to use on cell cultures. Antibiotics were not present in medium used for the propagation of the cell lines.

Culture medium used for transport of fetal tissues to the Cell Culture Laboratory was comprised of MEM supplemented with BFS at 5% concentration and the antibiotics: penicillin 100U/ml., neomycin 20γ/ml., streptomycin 50γ/ml. and fungizone 2.5γ/ml. Medium used for the maintenance of cell cultures in 16 × 150 mm tubes, 60 mm plates or 75 cm² flasks for tests on virus susceptibility and for tissue culture tests for adventitious agents was comprised of MEM supplemented with BFS 1%, peptone 0.1% and human serum albumin 0.5% final concentration ($BFS_1$ MEM) and the antibiotics above. These same antibiotics were also incorporated into the growth medium used for initial explanation of fetal tissues then omitted during the subsequent development and propagation of the cell cultures.

Culture Methods

Fetuses were removed by caesarian section and fetal organs were taken for culture. Fetal tissues were minced with scissors, rinsed with phosphate buffer solution (PBS) and treated for 4 successive 20-minute periods of magnetic stirring with warm (37° C) Bacto trypsin 0.25% 1:250, Difco Laboratories, Detroit, Michigan, in 0.05M TRIS buffered isotinic saline solution containing glucose at 1.0 gm/liter. Collagenase at 0.01% was incorporated into the trypsin solution for dispersal of lung and other tissues, and 0.25% pancreatin in PBS was also used.

Cells collected after the first 20 minutes were discarded; subsequent collections were passed through a stainless steel sieve, centrifuged at 1000 rpm for 10 minutes, washed with PBS and resuspended in culture medium. Cell concentrations were determined by direct counts in a hemocytometer, diluted as desired and seeded into culture flasks.

Skin, muscle and heart tissues were cut into 0.5 to 1.0 mm fragments in culture medium and approximately 15 fragments explanted directly into each culture flask wetted with medium. Fragments were allowed to drain onto the floor of the inverted flasks for 1 to 3 hours before adding additional culture medium. Culture flasks used in the establishment and maintenance of the cell strains were 75 cm² plastic, screw-cap flasks containing 25 ml. of medium. These were incubated at 37° C with slightly loose caps in a Wedco humidified incubator provided with 5% $CO_2$ in air environment. Cultures received a medium change or were subcultured each 3 to 4 days. Subculturing was performed on near-confluent to confluent culures by rinsing monolayers twice with 5 ml. each time of crystalline trypsin 0.01% in Medium 199. Flasks were then incubated at 37° C for 15 minutes or until cell monolayers were loosened. Cells were dispersed by pipette in 5 ml. culture medium and aliquots ranging from 0.5 to 2.5 ml. were seeded ino other flasks which received 25 ml. of additional medium. Cell concentrations were determined periodically on cultures selected for subculture.

Cell cultures of rhesus and AG monkey tissues were maintained in separate compartments of the same incubator or in separate incubutors, and were handled on separate occasions. All lines were maintained in duplicate, each series treated separately with correspondng lots of prepared media. Rigid aseptic techniques were adopted; surgical masks and gowns were worn when treating cultures and preparing media, and closed systems were used for dispensing medium into culture flasks. No other cell lines or viruses were brought into the laboratory where the cultures were maintained.

Determinations of Generation Time, Saturation Density, Plating Efficiency — Morphological Records.

These tests were performed at approximately each 5th passage on actively multiplying cells cultures. To determine generation times and saturation density, 100,000 cells in 4 ml. of MEM containing BFS at 10% concentration ($BFS_{10}MEM$) were seeded into 15 to 21 plastic (25 cm$^2$) flasks and incubated at 37° C in 5% $CO_2$ in air for 3 weeks. Cultures received a medium renewal each 2 to 3 days and 2 or 3 cultures were prepared at this time for enumeration of total cell nuclei. The numbers of nuclei per culture were plotted against hours of incubation on semilogarithmic graph paper and generation times determined for the 2 to 3 day interval during which the culture was growing at the maximum rate by the following formula:

$$\frac{\log_{10} \text{of } 2.0 \times t2 - t1}{\log_{10} \frac{(\text{No. of nuclei at } t2)}{(\text{No. of nuclei at } t1)}} = \text{generation time}$$

The number of cell doublings during this period (t2-t1) could be determined by the following formula:

$$\frac{\log_{10} \frac{(\text{No. of nuclei at } t2)}{(\text{No. of nuclei at } t1)}}{\log_{10} \text{of } 2.0} = \text{No. of doublings}$$

and subsequently:

$$\frac{t2 - t1}{\text{No. of cell doublings}} = \text{generation time}$$

Saturation density was taken as the maximum number of cell nuclei per culture obtained during the 3 week culture period and evident at the beginning of the plateau of the growth curve.

Plating efficiency tests, a measure of the percentage of cells capable of multiplying and forming macroscopic colonies in the absence of feeder cells, was determined by seeding 60 mm plastic plates, 3 each, with $5 \times 10^3$, $2 \times 10^3$ and $5 \times 10^2$ cells. Culture plates were incubated at 37° C in a humidified, 5% $CO_2$ in air incubator and received a medium change each 7 days. Plates were fixed and stained on the 16th day with Leishman's stain in methanol and the number of macroscopical colonies counted. Results were expressed as the percentage ratio of number of colonies formed to the number of cells inoculated.

For permanent records of morphology and cytological study, cells were cultured 48 hour in $16 \times 150$ mm tubes flattened on one side to accommodate a $12 \times 40$ mm coverslip. Coverslips were fixed with Bouin's fixative, stained with Giemsa and mounted in Permount.

One commercial lot of BFS and MEM was used in preparation of $BFS_{10}MEM$ medium used for all tests of generation time, plating efficiency and satuation density.

Freeze Preparation of Cell Lines

All excess cultures, often primary, and after each 1 to 3 passages, were prepared for preservation by freezing and storage at liquid nitrogen temperatures. Methods of freezin were similar to those described previously for the preservation of human diploids cel lines. Cells from 1 to 3 culture flasks were dispersed with crystalline 0.01% trypsin, centrifuged in $BFS_{10}MEM$ medium, resuspended in 1 ml. MEM containing BFS at 15 to 20% and glycerol at 5 to 10% concentration, and sealed in a 1.2 ml. glass ampoule. Ampoules were held at +4° C, then frozen at a controlled rate of 1° C per minute either in an Alcohol-$Co_2$ bath or in a liquid nitrogen Linde BF-3 freezer. Less well-controlled freezing rates were obtained by use of the Linde BF-5 freezer, which is a polystyrene plug designed to fit into the opening of the 35 liter nitrogen Linde LNR-35 refrigerator. Ampoules were removed from the freezers when the temperature of the freezing unit reached −60° C and were stored immediately in the LNR-35 refrigerator at −185° to −196° C.

In experimental studies, demethylsulfoxide (DMSO) at 5 or 10% concentration was substituted for glycerin, and Bactopeptone, human serum albumin, mesoinositol and polyvinylpyrrolidone (PVP) were incorporated into the glycerol freezing medium and tested for protective effect against freezing damage.

Frozen ampoules were thawed by quick immersion and agitation in a 43° C water bath for 30 seconds. They were sterilized with 95% ethyl alcohol, held in sterile gauze and snapped open. The contents of each ampoule was diluted 1:9 with $BFS_{10}MEM$ medium, centrifuged and resuspended in 25 to 50 ml. medium for inoculation into 75 cm$^2$ culture flasks. Viability was determined by direct cell count in a hemocytometer using 0.01% eosin and expressed as the number of cells per 100 counted that were unstained.

Oncogenic Tests

Tests for oncogenicity were performed in Syrian hamsters by inoculating cells of actively peroliferating lines in the 10th and 20th passage into the check pouch of adult hamsters by the technique of Handler and Foley and subcutaneously into 1-day old treated with rabbit anti-hamster lymphocyte serum (ALS).

ALS was prepared by injecting each of three 6 lb. New Zealand white rabbits subcutaneously with $10^9$ viable adult Syrian hamster thymocytes in Freund's complete adjuvant on day 0, followed by two intravenous injections of 3 to $5 \times 10^8$ thymocytes given on day 14 and on day 28. Rabbits were bled 7 days after the last injection. Sera were heated at 56° for 30 minutes and tested for hemolytic and cytotoxic antibody activity. Hemolytic titers were determined by adding 0.1 ml. of each serum dilution to 0.8 washed homologous erythrocytes at 5 million/ml. in veronal buffered diluent. One tenth ml. of guinea pig complement was added after 10 minutes and tubes were read for hemolysis following 45 minutes incubation in a 37° C water bath. Aliquots of ALS were also tested for hemolysis after absorption overnight with 20% by volume of homologous erythrocytes. As none of the ALS had significant hemolytic activity (<1:20), it was used unabsorbed in oncogenic tests in 1-day old hamsters.

Cytotoxic antibody test on ALS were performed by incubating 0.1 ml. of each serum dilution with 5 million viable hamster thymocytes in 0.8 ml. of NCTC 109 medium and 0.1 ml. guinea pig complement. Tests were read following incubation at 37° C for 45 minutes by direct count of living and dead cells in a hemocytometer using 0.01% eosin. Endpoints were expressed as that serum dilution which killed approximately 50% of the cells. Cytotoxic antibody titers of the ALS prepared as described ranged from 1:320 to 1:640.

Used as a positive control for all oncogenic tests were human epidermoid carcinoma cells, strain KB, received from Dr. George Foley, Children's Cancer Research Foundation, Boston. Negative controls were cells from primary cultures of rhesus monkey kidney (RMK); cells from primary cultures of Syrian hamsters embryos and human diploid fibroblasts, Line WI-38, were also used as controls in tests performed in 1-day old hamsters. Cells to be inoculated were harvested from culture flasks using 0.05% trypsin in TRIS buffered saline, centrifuged and suspended in MEM to a final concentration of $2.5 \times 10^5$ cells/0.1 ml.

One tenth ml. of each cell suspension was inoculated intradermally into each cheek pouch of 6 anesthetized 60–70 gram hamsters. Three of these hamsters received 0.05 ml. containing 2.5 mg. of cortisone acetate subcutaneously on the day the cells were inoculated and twice weekly thereafter during a 4 week observation period. Hamsters were anaesthestized and pouches examined twice a week for the development of nodules. Nodules were measured and recorded, and excised at 4 weeks for histological study.

One tenth ml. of each cell suspension was also inoculated subcutaneously into each of 7 or more 1-day old hamsters, the cells being deposited along the back and neck region. The new-born hamsters also received 0.05 ml. intraperitoneally of undiluted ALS. In preliminary studies on the development of the test, doses of KB cells ranging from $5 \times 10^5$ to $5 \times 10^4$ were inoculated and hamsters received 1 to 5 total injections of ALS or normal rabbit serum given on the day of cell inoculation and at 3 to 7 intervals thereafter. Hamsters were observed for tumors twice a week during 4 weeks; tumors were measured and recorded and occasionally excised for histological examination.

Tests for Adventitious Agents

Actively proliferating cell lines were tested when possible as primary cultures and at the 10th and 20th passage for adventitious agents. Cultures for testing were usually prepared from cell suspension which had been harvested and pooled from each of the duplicate series of the cell line.

Frozen-thawed cells and spent medium, taken about 17 days after planting, were tested for viruses as specified in Biological Products, USPHS Regulations, title 42, part 73.113(d), by inoculation of 10 ml. into flask cultures of each of the following primary cells: RMK, CMK, rabbit kidney and human amnion, as well as cultures of human diploid fibroblasts, line Led 130. Cultures were observed for 2 weeks; CMK cells and fluids were blind passed once into other CMK cultures and subcultures were held for 2 weeks.

Frozen-thawed cells and spent media were also inoculated both intraperitoneally and intracerebrally into rabbits, adult male and suckling mice according to USPHS Regulations, title 42, part 73.114(a) except that 3 rabbits only were used and each received 0.1 ml. intracerebrally and 10.0 ml. intraperitoneally.

Cells and spent media were inoculated into embryonated chicken eggs via the yolk sac, allantoic sac and chorioallantoic membrane (CAM) according to the USPHS Regulations, title 42, part 73.142, Safety Test a-5. Five tenths ml. was inoculated into the allantoic cavity of each of ten 9-day old, 0.5 ml. into the yolk sac of each 6-day old and 0.2 ml. onto the CAM of each ten 6-day old embryonated eggs. Eggs were incubated 7 days. Embryos dying after 48 hours were tested for lethal agents by passing 0.3 ml. of allantoic fluid from those inoculated by the yolk sac route and 0.3 ml. of a 10% CAM suspension from those inoculated by the CAM route to 6 embryonated eggs each, using their respective routes of inoculation. Allantoic fluids from embryos inoculated by the allantoic route were also tested for hemagglutination (HA) of chicken erythrocytes. A test was considered acceptable if 80% of the embryos survived and none showed HA activity or other evidence of a transmissible agent.

Hemadsorption tests were performed on tube cultures of cells to be tested at 6, 10, and 14 days after planting. At these times cell monolayers were washed with PBS, incubated at +4° C for 20 minutes with 1.0 ml. of a 0.4% suspension of guinea pig erythrocytes, again washed and examined microscopically for hemadsorption.

Cell lines seeded in 60 mm plastic plates were examined for intranuclear inclusion bodies with a fluorescent microscope following fixation with methanol and staining with acridine orange at pH 5.2.

Cells were also tested for the presence of CMV by the indirect fluorescent antibody test in 60 mm plastic plates essentially as described under *Serological Tests*, except that a rhesus monkey serum known to be positive for antibody to CMV was used for the initial overlay.

Cells of lines to be tested were examined by autoradiographic techniques for intracytoplasmic incorporation of thymidine. For this test, cells were cultured on 3 × 1 inch slides and incubated 18 hours in medium tritiated thymidine, specific activity: 6.0 C/mMole. Purchased from Schwarz BioResearch, Orangeburg, New York, at 0.5 microcuries/ml. Slides were rinsed with PBS, fixed in Bouin's dried and coated with Kodak NTB.3 emulsion. After exposure in the dark, they were developed, stained with Giemsa and examined microscopically for tritium label.

Actively proliferating cell lines were also tested for sterility at each 5th passage essentially as described in USPHS Regulations, title 42, part 73.73 for bacteria and fungi and part 73.74a for mycoplasma. A modification of the test for mycoplasma has been recently adopted and consists of inoculating test samples in 0.1 ml. of volumes to each of four 60 mm plates containing Hayflick's agar medium, and in 1.0 ml. volumes to 2 tubes containing 10 ml. each of Hayflick's broth medium. One tube is incubated aerobically, the other anaerobically. After 7 days' incubation, plates are read for mycoppasms; samples from the broth tubes are sub-inoculated in 0.1 ml. volumes to each of teo Hayflick agar plates, which are incubated aerobically and anaerobically for an additional 7 days and read for the presence of mycoplasma. A positive control (M. pneumoniae) is run with each test.

Tests for Virus Susceptibility, Virus Yields

Viral susceptibility tests on cell lines were performed when possible on primary cultures and at each fifth passage, using the following 6 viruses: poliovirus type II, Sabin vaccine strain p 712; human adenovirus type 3, J. F. strain isolated by Dr. R. J. Huebner; rhinovirus type 2, HGP Salisbury strain; rubella, M33 strain of Parkman, et al., vaccinia, commercial calf lymph vaccine propagated on CAM of embryonaed eggs; and measles, Edmonston strain obtained from Dr. John Enders, Children's Hospital Medical Center, Boston.

At the 10th and 20th passage, cell lines were also tested for susceptibility to the following additional viruses: poliovirus type I LSc and poliovirus type III Leon, Sabin vaccine strains; human adenovirus type 4 received from Col. T. O. Berge, Walter Reed Armed Forces Institute of Research; human adenovirus type 7, L.L. strain isolated by Dr. R. J. Huebner; human parainfluenza viruses types 1, 2 and 3 obtained from Dr. R. M. Chanock of the National Institute of Allergy and Infectious Diseases; influenza, Hong Kong strain type $A_2$./Aichi/68 obtained from Dr. John Wagner, Division of Biologics Standards; herpes simplex HF strain obtained from American Type Culture Collection; mumps, Angela strain isolated in these laboratories by Dr. C. P. Cerini from a five year old girl with the disease; coxsackie type A9 obtained from the American Type Culture Collection; human cytomegalovirus obtained from Mrs. Hope Hopps, Division of Biologics Standards, and rabies virus, Lederle HEP strain.

All tests were preformed on 48-hour cultures in 16 × 150 mm tubes, except for the test for rabies virus susceptibility which was carried out in 60 mm plastic plates. Four 10-fold dilutions of each virus was prepared in Earle's balanced salt solution containing lactalbumin hydrolysate at 0.5% concentration and inoculated in 0.1 to 0.2 ml. amounts to each of three cultures. Control virus titrations were sometimes performed simultaneously in primary cultures of RMK for the polioviruses, adenoviruses types 3 and 7, influenza and parainfluenza viruses, coxsackie A9 and vaccinia; in primary cultures of CMK for adenovirus type 4, mumps and rubella viruses; in primary cultures of chick embryo for rabies virus; in cell cultures of BS-C-1for herpes simplex and measles viruses and in cell cultures of Led 130 for CMV and rhinovirus HGP.

Cultures inoculated with CMV, measles and rubella viruses were observed during 14 days incubation; those inoculated with parainfluenza virus types 1 and 2 during 10 days; and those inoculated with influenza virus during 5 days incubation. Cultures for all other viral titrations were incubated for 7 days.

Endpoint determinations for the replication of most viruses were viral cytopathic effects (CPE); influenza and parainfluenza virus replication was determined by the guinea pig erythrocyte hemadsorption test, rabies virus by the direct fluorescent antibody test and rubella virus by the ECHO-11 virus interference test. In the latter test, cultures inoculated with dilutions of rubella virus were challenged at 12 days with 1000 to 10,000 $TCID_{50}$ doses of ECHO-11 virus and read for CPE 2 days later. $TCID_{50}$ titers were calculated by the method of Reed and Muench and expressed as the reciprocal $log_{10}$/ml. of the highest dilution of virus producing detectable virus replication in cells of the line being tested.

Tests for yields of poliovirus types I and II and of rubella virus were performed in 75 $cm^2$ flask cultures of the cell strains. Confluent cultues were replenished with $BFS_1MEM$ medium and each received 1.0 ml. of either a 1:60 dilution of poliovirus having a titer of $10^{6.0}$ $TCID_{50}$/ml. or rubella virus having a titer of $10^{4.5}$ $TCID_{50}$/ml. Cultures were placed at 36° C for 2 hours, washed twice each with 10 ml. and finally replenished with 25 ml. $BFS_1MEM$ medium. Cultures inoculated with polioviruses were observed during 3 to 4 days incubation and frozen when extensive CPE was evident. Cultures inoculated with rubella virus received a medium change on the 7th and 14th day and were frozen after 21 days incubation. Titration of the fronzen-thawed culture harvests were performed in the control culture systems described above for these viruses, using 8 tubes per virus dilution.

Chromosome Analysis

Permanent slides were prepared for examination of metaphase chromosomes of cell lines at approximately each fifth passage by the basic procedures of Moorhead and Nowell. Forth-eight hour flask cultures were treated during the last 4 or 12 hours of incubation with colcemide at 0.1μg/ml. Cells were collected by treatment of cultures with 2 ml. of trypsin 0.25% in TRIS buffered saline at 37° C or by vigorously shaking the culture flasks, and were sedimented by centrifugation. Following a 10 minute hypotonic treatment with sodium citrate 1.0% in distilled water, the cells were fixed during 30 minutes and 3 changes with a mixture of acetic acid 1 part: absolute methanol 3 parts. Drops of cell suspension were rapidly dried by warming onto chilled slides. Slides were treated with hydrochloric acid at 60° C for 10 minutes, washed in distilled water, stained with Giemsa, dehydrated and mounted with Preservaslide (synthetic resin mounting medium, Matheson, Coleman & Bell, Rutherford, N.J.).

Permanent slides of cells in metaphase have also been prepared from primary kidney cell cultures prepared from young, 2 to 3 year old rhesus monkeys. Cultures were treated as described above on the 4th or 5th day after seeding.

Attempts have also been made to culture leucocytes from peripheral blood of young rhesus monkeys for analysis of metaphase chromosomes. As rhesus monkey blood erythrocytes do not readily sediment upon standing, these were agglutinated by the addition of phytohemagglutinin M (0.2 ml. for 8 ml. blood for 10 minutes) and the mixture centrifuged at 200 rpm for 4 minutes. Good recoveries of leucocytes were also obtained by overlaying equal volumes of heparinized blood onto a mixture of methylcellulose and sodium metrizoate as described by Hulliger and Blazkovec.

Leucocytes were recovered from the upper layers of sedimented blood by centrifugation, then washed with PBS and resuspended at 1 to 3 × $10^6$cells/ml. in MEM, LAPAGT, 199 or 1640 medium each supplemented with human or bovine serum at 20%, phytohemagglutinin P at 0.01% concentration and antibiotics. Cells suspended in culture medium were incubated in 10 ml. amounts in 1 oz. screw cap vials at 37° C in 5% $CO_2$ in air for 3 to 7 days. They were prepared for examination of the metaphase chromosomes as described for human leucocyte cultures by Moorhead and Nowell.

Where mitotic figures were plentiful and metaphase chromosomes well spread, the range of ploidy was determined by rough counts on 250 cells at random under 250X magnification. An additional 50 cells were selected and these were examined under 1000X magnification for exact number of chromosomes, for breaks or other chromosome aberrations. The location of metaphases with aberrations and those optically good were noted and photographed, using polaroid 4 × 5 inch P/N film type 55.

RESULTS

Twenty-four cell lines were established from fetal tissues of rhesus and AG monkeys and these were assessed periodically for adventitious agents, virus susceptibility, cytogenetic characteristics and growth potential. Cell lines which appeared promising in these areas were selected for more detailed study including tests for tumorigenicity and preservation by freezing.

Epithelial cell lines developed from kidney tissue generally grew well through 6 culture passages and then declined in growth; resumption of growth was usually accompanied by pronounced cytogenetic changes.

Fibroblastic lines established from lung, heart, skin and muscle were characterized by a finite life consisting of active cell multiplication varying from 10 to 56 passages, followed by a period of growth decline and senescence during 3 to 36 further passages. Fibroblasts derived from lung had the greatest potential in terms of growth vigor and total doublings, and fibroblastic cells from rhesus monkeys were usually capable of more doublings than similar lines derived from AG monkeys.

TABLE 2

HISTORY AND CULTURAL CHARACTERISTICS OF MONKEY DIPLOID CELL LINES

|  | DBS-FRhL-2 LUNG, RHESUS MONKEY FETUS, MALE | DBS-FCL-1 LUNG, AG MONKEY FETUS, MALE | DBS-FCL-2 LUNG, AG MONKEY FETUS MALE |
|---|---|---|---|
| ORIGIN FINITE LIFE | 248 GM. | 135 DA. GESTATION | 141 DA. GESTATION |
| Active Growth: | 6 Mo. 44 Passages | 5 Mo. 35 Passages | 5 Mo. 40 Passages |
| Growth Decline and Senescence: | 3 Mo. 7 Passages | 4 Mo. 18 Passages | 4 Mo. 22 Passages |
| Total Passages: | 51 | 53 | 62 |
| Population Doublings: | 74 | 60 | 67 |
| Doubling Time: | 33 Hrs. | 33 Hrs. | 40 Hrs. |

One line of rhesus lung (DBS-FRhL-2) and two lines of AG lung (DBS-FCL-1 and DBS-FCL-2) were propagated through 60—74 population doublings. DBS-FRhl-2 cells originated from a 248 gm. male rhesus fetus and the cells multiplied at a rapid unchanging rate during approximately 6 months and 44 culture passages. During this time cultures were subdivided 1:1 each 3-4 days and population doubling times averaged 33 hours. At passage 44, which represented approximately 67 doublings, the cells entered a period of growth decline, lasting about 3.0 months, and ceased to multiply after a total of 51 passages and 74 population doublings.

DBS-FCL-1cells originated from a 135 day, male AG fetus. These cells multiplied vigorously through 5 months and 35 culture passages, and then more slowly for approximately 4 months. The cells ceased to multiply after 53 culture passages and 60 population doublings.

DBS-FCL-2 cells originated from a 141 day, male, AG fetus. These cells multiplied vigorously through 5 months and 40 culture passages, and then entered a period of growth decline. DBS-FCL-2 cells could not be propagated beyond 62 culture passages, and approximately 67 population doublings.

The morphology of all 3 cell lines was fibroblastic. During active cell multiplication, the cells grew in uniform monolayers as spindle to oval-shaped cells, loosely connected by cytoplasmic processes.

In senescent cultures of DBS-FRhL-2cells in passage 50, no mitotic figures were seen and many cells developed cytoplasmic vacuoles. Multinucleate cells and micronuclei formation were also observed.

TABLE 3

CYTOGENETIC DATA ON DBS-FRhL-2 CELLS

| CULTURE PASSAGE | HYPER-DIPLOID (%) | POLYPLOID (%) | BREAKS & GAPS (%) | STRUCUTRAL ABNORMAL-ITIES (%) |
|---|---|---|---|---|
| 24-26 | 1/113 (0.9) | 6/698 (0.9) | 3/113 (2.7) | 0/113 (0) |
| 36 | 0/163 (0) | 7/999 (0.7) | 11/163 (6.8) | 0/163 (0) |
| 45 | 3/51 (5.9) | 61/404 (15.1) | 1/51 (2.0) | 1/51 (2.0) |

The karvology of the cell lines was studied by the air drying technique. The data here show that DBS-FRhL-2cells were predominantly diploid through the passages examined. The majority of the cells were in the diploid range; few huyperdiploid cells were found and an increase in polyploidy occurred only in aging cultures, similar to that described from human diploid cells. The structural abnormalities observed in again cultures were unstable dicentric forms.

TABLE 4

| | CULTURE PASSAGE | KARYOLOGICAL DATA ON DBS-FCL-1 AND DBS-FCL-2 CELLS | | | | | | |
|---|---|---|---|---|---|---|---|---|
| | | HYPER-DIPLOID (%) | | POLYPLOID (%) | | BREAKS AND GAPS (%) | | STRUCTURAL ABNORMALITIES (%) |
| DBS-FCL-1 | 22 | 3/126 | | 36/763 | (4.7) | 6/126 | (4.8) | 0/126 (0) |
| | 24–47 | 45/1,233 | (3.6) | 160/6,044 | (2.6) | 79/2,233 | (3.5) | 48/2,223 (2.2) |
| | 23 | 0/54 | (0) | 9/425 | (2.1) | 4/54 | (7.4) | 0/54 (0) |
| DBS-FCL-2 | 32 | 0/57 | (0) | 4/292 | (1.3) | 6/57 | (10.5) | 0/57 (0) |
| | 44 | 0/60 | (0) | 6/208 | (2.8) | 8/60 | (13.3) | 0/60 (0) |

Table 4 presents a summary of cytogenetic data on DBS-FCL-1and DBS-FCL-2. The majority of the cells are in the diploid range, with few cells showing hyperidploidy through the passages examined. An increased frequency of chromosome abnormalities was observed only in again cultures and there were unstable dicentric chromosomes or exchange configurations.

TABLE 5

VIRUS SUSCEPTIBILITY OF DBS-FRhL-2

| CULTURE AGE | POLIO- T | II | III | ADENO- 3 | 7 | PARA- 2 | 3 | INFLU- A-2 | HERPES PLEX | MUMPS | RHINO HGP | RH- LA | COX- A-9 | VAC- IA | LES |
|---|---|---|---|---|---|---|---|---|---|---|---|---|---|---|---|
| 14 | 4.4* | 5.2 | 6.9 | 2.9 | 1.7 | 4.4 | 3.2 | 1.2 | 3.2 | 3.2 | 5.9 | 4.2 | 7.2 | 8.4 | 2.2 |
| 20 | 6.2 | 6.4 | 7.4 | 1.2 | 1.2 | 2.2 | 6.9 | 2.4 | 1.2 | 3.9 | 4.2 | 3.2 | 7.2 | 8.9 | 2.9 |
| 30 | 6.0 | 6.0 | 6.9 | 2.4 | 1.2 | 2.2 | 6.9 | 2.4 | 1.2 | 2.2 | 5.2 | 4.2 | 6.9 | 8.9 | 4.2 |
| CONTROL (AVE) | 5.7 | 6.1 | 7.0 | 4.2 | 3.7 | 4.0 | 4.3 | 5.5 | 5.2 | 4.9 | 5.4 | 3.6 | 6.8 | 8.0 | 5.8 |

*Reciprocal $Log_{10}$ of the $TCID_{50}$/ml.

Viral susceptibility tests were performed on 48 hour cultures of the cell lines. Simultaneous titrations of the viruses were also performed in susceptible control cell culture systems. The polioviruses, influenza, the parainfluenzas, human adenoviruses, Coxsackie A9, and vaccinia virus were titrated simultaneously in primary rhesus monkey kidney; rubella and mumps in primary AG monkey kidney; herpes simplex and measles virus in AGMK BSC-1cells; and rhinovirus in human diploid cell strain Led-130. As shown in Table 5, DBS-FRhL-2cells are comparable to control culture systems in sensitivity to the polioviruses, parainfluenza virus type 3, rhionovirus, rubella, Coxsackie A9 and vaccinia virus.

TABLE 7

RUBELLA VIRUS PRODUCTION IN RHESUS LUNG DBS-FRhL-2

| DAYS POST INFECTION | VIRAL TITER* IN FRhL-2 | VIRUS SEED REFERENCE |
|---|---|---|
| 11 | 5.5 | 3.7 |
| 15 | 6.0 | 4.3 |
| 18 | 4.5 | 4.5 |
| 22 | 6.0 | 5.0 |
| 25 | 5.3 | 5.0 |
| 28 | 5.5 | 4.2 |
| 31 | 6.0 | 4.2 |
| 35 | 5.3** | 5.0 |

*$Log_{10}$ of the $TCID_{50}$/ml.
**Cells destroyed by virus.

Tests on rubella virus production were performed in DBS-FRhL-2cultures which were infected with $10^{4.0}$ T.C.I.D.$_{50}$ infectious doses of rubella and incubated at 36° C. Culture medium was replaced each 3–4 days and infected fluids were titrated for viral activity simultaneously with a rubella virus reference seed grown in primary cultures of AG monkey kidney. A slow, progressive cytopathic effect of the virus destroyed the cells in infected cultures after 35 days incubation. During this period, the cultures continued to produce virus with titers comparable to those obtained in control culture systems.

TABLE 6

VIRUS SUSCEPTIBILITY OF DBS-FCL-1 AND DBS-FCL-2

| CULTURE PASS AGE | POLIOVIRUS I | II | III | ADENOVIRUS 3 | 7 | PARAINFLUENZA 2 | 3 | INFLUENZA A-2 | HERPES SIMPLEX | MUMPS | RHINO VIRUS HGP | RUBELLA | COXSACKIE A-9 | VACCINIA | MEASLes |
|---|---|---|---|---|---|---|---|---|---|---|---|---|---|---|---|
| DBS FCL-1 | | | | | | | | | | | | | | | |
| 10 | 6.2* | 6.2 | 6.4 | 3.2 | 3.2 | 0.7 | 6.9 | 2.2 | <4.2 | 4.7 | 5.7 | 4.4 | 6.9 | 8.4 | 4.4 |
| 31 | 4.4 | 4.4 | 6.4 | 2.9 | 2.4 | 1.2 | 3.4 | 1.2 | 6.2 | 3.2 | 5.9 | 2.9 | 7.2 | 8.2 | 4.2 |
| 40 | 4.4 | 4.4 | 7.2 | 2.9 | 3.2 | 1.2 | 3.2 | 1.2 | 5.4 | 3.2 | 5.9 | 4.2 | 6.4 | 7.4 | 3.7 |
| DBS FCL-2 | | | | | | | | | | | | | | | |
| 10 | 5.7 | 5.7 | 6.4 | 2.4 | 2.2 | 0 | 6.4 | 1.2 | 6.9 | 4.4 | 5.2 | 3.2 | 6.7 | 8.4 | 4.4 |
| 29 | 5.2 | 6.7 | 7.0 | 3.2 | 3.2 | 0 | 5.7 | 1.2 | <6.9 | 2.2 | 4.2 | 2.9 | 6.4 | 7.9 | 3.9 |
| 40 | 5.2 | 5.2 | 6.2 | 3.2 | 3.2 | 1.2 | 5.2 | 1.2 | 6.7 | 2.2 | 3.2 | 3.2 | <5.2 | 8.4 | 4.4 |
| CONTROL (AVE) | 5.7 | 6.1 | 7.0 | 4.2 | 3.7 | 4.0 | 4.3 | 5.5 | 5.2 | 4.9 | 5.4 | 3.6 | 6.8 | 8.0 | 5.8 |

*Reciprocal $Log_{10}$ of the $TCID_{50}$/ml.

DBS-FCL-1 and DBS-FCL-2cells showed a spectrum of virus susceptibility similar to that of DBS-FRhL-2. These AG monkey lines are sensitive to the polioviruses, parainfluenza virus 3, rhinovirus, rubella, Coxsackie A9, and vaccinia. They are also sensitive to herpes simples.

The 3 diploid cell lines described were tested at several passage levels for advantitious agents as specified by USPHS Regulations for safety testing of biological products. This included direct tests on the cell for hemadsorbing agents using guinea pig red cells, tests for nuclear inclusions using acridine orange stain, and fluorescent antibody tests for specific viral antigens of simian viruses: $SV_{40}$, $SV_5$, and CMV. The cells were also tested for immunofluorescence to possible antibodies present in maternal monkey serum. All tests were negative.

Cells and spent media were tested for bacteria, fungi, and mycoplasma in suitable media, and for the presence of viruses by inoculation into cultures of primary AG monkey kidney, rhesus monkey kidney, rabbit kidney and human amnion, as well as into cultures of human diploid cells (Led-130) and an AGMK cell line (BS-C-1). In vivo tests were also performed by inoculating cells and spent medium into embryonated hen's eggs, adult male, suckling mice and rabbits. All tests were negative.

Tests for tumorigenicity were performed on the cell lines during active growth as well as during their declining growth phase. Cells were inoculated intradermally into the cheek pouch of cortisone-treated adult Syrain hamsters, as well as subcutaneously into newborn hamsters treated with antilymphocytic serum. None of the monkey diploid cell lines produced tumors in these heterologous hosts. Additional tests using the antilymphocytic-treated newborn homologous monkey are in progress, and results to date show no tumor-producing potential for these cells.

Cells which have been frozen in medium containing 7.5% glycerine or dimethyl-sulfoxide and stored in liquid nitrogen for periods up to 12 months have been recovered with 60-75% viability. Recovered cultures of these cell lines have shown no changes in virus susceptibility, cytogenetic or growth characteristics. The equivalent of 500 cultures each containing 3 million cells at passage 5 have been prepared and frozen for the cell lines described.

Samples of the cell lines have been deposited with the American Type Culture Collection for storage and distribution upon request. Requests can be made to the Division of Biologics Standards of the Department of Health, Education and Welfare. Additionally, two of the cell lines have been submitted to the ATCC for inclusion in their regular stock on 15 October 1971, and bear the following numbers: (DBS-FR hL-2) - (CL 160); (DBS-FCL-1) - (CL 161).

It should be apparent from the foregoing detailed description that the objects set forth hereinabove have been successfully achieved. Moreover, while there is shown and described present preferred embodiments of the present invention, it is to be distinctly understood that the invention is not limited thereto but maybe otherwise variously embodied and practiced within the scope of the following claims.

What is claimed is:

1. A cell culture for virus vaccine production comprising a sub-human primate diploid cell line bearing ATCC Accession No. CL-160 and a nutrient medium therefor.

* * * * *